(12) United States Patent
Miyagi et al.

(10) Patent No.: US 7,883,459 B2
(45) Date of Patent: Feb. 8, 2011

(54) ENDOSCOPE AND METHOD FOR REPAIRING THE SAME

(75) Inventors: Masaaki Miyagi, Hachioji (JP); Hiroki Moriyama, Akishima (JP); Seisuke Takase, Hachioji (JP)

(73) Assignee: Olympus Corporation, Tokyo (JP)

(*) Notice: Subject to any disclaimer, the term of this patent is extended or adjusted under 35 U.S.C. 154(b) by 607 days.

(21) Appl. No.: 11/654,931

(22) Filed: Jan. 18, 2007

(65) Prior Publication Data
US 2007/0118013 A1 May 24, 2007

(30) Foreign Application Priority Data
Jul. 26, 2004 (JP) ............................. 2004-217881

(51) Int. Cl.
*A61B 1/06* (2006.01)

(52) U.S. Cl. ................... 600/129; 600/130; 600/164; 600/172; 600/175; 600/176; 600/182

(58) Field of Classification Search ............... 600/129, 600/179–177, 182, 127, 164, 171, 172, 174, 600/176
See application file for complete search history.

(56) References Cited

U.S. PATENT DOCUMENTS

| | | | | |
|---|---|---|---|---|
| 5,315,383 | A * | 5/1994 | Yabe et al. | 348/68 |
| 5,614,943 | A * | 3/1997 | Nakamura et al. | 348/72 |
| 2001/0003142 | A1* | 6/2001 | Koshikawa | 600/177 |
| 2003/0025789 | A1* | 2/2003 | Saito et al. | 348/76 |
| 2003/0123825 | A1* | 7/2003 | Sanso | 385/117 |
| 2007/0055106 | A1* | 3/2007 | Moriyama | 600/178 |

FOREIGN PATENT DOCUMENTS

| | | |
|---|---|---|
| EP | 1 764 029 A1 | 3/2007 |
| EP | 2 011 428 A1 | 1/2009 |
| JP | 6-82619 | 11/1994 |
| JP | 10-211165 | 8/1998 |
| JP | 10-211167 | 8/1998 |
| JP | 10-288742 | 10/1998 |
| JP | 11-032977 | 2/1999 |
| JP | 11-125773 | 5/1999 |
| JP | 2001-258823 | 9/2001 |

OTHER PUBLICATIONS

Extended Supplementary European Search Report dated Feb. 3, 2010.

* cited by examiner

*Primary Examiner*—Matthew J Kasztejna
(74) *Attorney, Agent, or Firm*—Scully, Scott, Murphy & Presser, P.C.

(57) ABSTRACT

Distal ends of the LG fiber bundles are held in a state of being inclined outwardly with respect to an insertion direction of the distal end rigid portion, an observation hole for holding the image-pickup unit is formed at the distal end rigid portion, illumination holes for holding the distal ends of the LG fiber bundles are formed around the observation hole, the illumination holes are inclined outwardly with respect to an insertion direction of the distal end rigid portion, extended lines of inclined angles of the illumination holes are set to pass through backward of the observation hole, and a space after removal of the image-pickup unit from the observation hole is secured as a space for withdrawal of the LG fiber bundles.

4 Claims, 6 Drawing Sheets

ENDOSCOPE AND METHOD FOR REPAIRING THE SAME

CROSS REFERENCE TO RELATED APPLICATION

This application is a continuation application of PCT/JP2005/013477 filed on Jul. 22, 2005 and claims benefit of Japanese Application No. 2004-217881 filed in Japan on Jul. 26, 2004, the entire contents of which are incorporated herein by this reference.

BACKGROUND OF THE INVENTION

1. Field of the Invention

The present invention relates to an endoscope including an observation optical system with wide viewing angle, and also relates to a method for repairing the endoscope.

2. Description of the Related Art

As is well-known, an endoscope is widely used in a medical field, and the like. The endoscope, for example, can provide observation of organs and the like within a body cavity by inserting an elongated insertion portion into the body cavity and various treatments using a treatment instrument inserted into a treatment instrument insertion channel as needed. A bending portion is formed at the distal end of the insertion portion, and the observation direction of an observation window at the distal end can be changed by operating an operation portion of the endoscope.

The conventional endoscope has an observation viewing angle of approximately 120 to 140 degrees, and an operator observes inside a body cavity with an observation image at the observation viewing angle. If the operator would like to observe a site outside a viewing field range during the observation in the body cavity, the operator observes the site by bending the bending portion.

Meanwhile, there have been proposed various endoscopes with wider observation viewing angle so as to observe a wider range.

For example, Japanese Patent Application Laid-Open No. 2001-258823 discloses an endoscope including at a distal end portion thereof an observation optical system with a wide observation viewing angle of approximately 140 to 210 degrees. In the endoscope disclosed in the publication, in accordance with the wider viewing angle of the observation optical system, a light guide fiber bundle for illuminating inside a body cavity is disposed such that the optical axis of a distal end portion of the bundle is inclined outwardly at a predetermined angle with respect to the optical axis of the observation optical system, in order to uniformly illuminate all over an observation site in the body cavity.

Incidentally, the light guide fiber bundle is connected as one fiber from a distal end of a universal cord connected to a light source device to an endoscope distal end portion in the endoscope. Therefore, when a part of the light guide fiber bundle is damaged, it is required to replace the whole of the light guide fiber bundle with a new one.

When replacing the light guide fiber bundle, an outer cover tube covering the endoscope distal end portion is removed at first, to expose the distal end portion of the light guide fiber bundle inserted inside the distal end portion of the endoscope, and then the distal end portion of the light guide fiber bundle fixed to a distal end rigid portion is detached by using a tool and the like. After that, the light guide fiber bundle is pulled out from the side of the universal cord. Next, a new light guide fiber bundle is inserted from the side of the universal cord, and a distal end of the bundle is attached to the distal end rigid portion by using a tool and the like, to be adhered and fixed thereto.

SUMMARY OF THE INVENTION

There is provided an endoscope including: a light guide fiber bundle for guiding illumination light from a light source; a wide-angle observation optical system for observing a subject illuminated with illumination light emitted from the light guide fiber bundle; and an endoscope distal end portion for holding a distal end portion of the light guide fiber bundle and a distal end portion of the observation optical system, the distal end portion of the light guide fiber bundle being held around the observation optical system in a state of being inclined outwardly with respect to an insertion direction of the endoscope distal end portion. The endoscope comprises an observation hole for holding the observation optical system, the observation hole being formed along the insertion direction of the endoscope distal end portion, and an illumination hole for holding the distal end portion of the light guide fiber bundle, the illumination hole being formed around the observation hole, in which the illumination hole is inclined outwardly with respect to the insertion direction of the endoscope distal end portion, an extended line of an inclined angle of the illumination hole is set to pass through backward of the observation hole, and an insertion and withdrawal direction of the distal end portion of the light guide fiber bundle is set to be in a space after removal of the observation optical system, the space being formed after the observation optical system has been removed from the observation hole.

According to the present invention, excellent advantages are expected, i.e., the light guide fiber bundle can be smoothly replaced without causing a damage thereto, fitting workability can be improved, etc.

DETAILED DESCRIPTION OF THE PREFERRED EMBODIMENT

Hereinafter, an embodiment of the present invention will be described with reference to the drawings.

Figure 1:
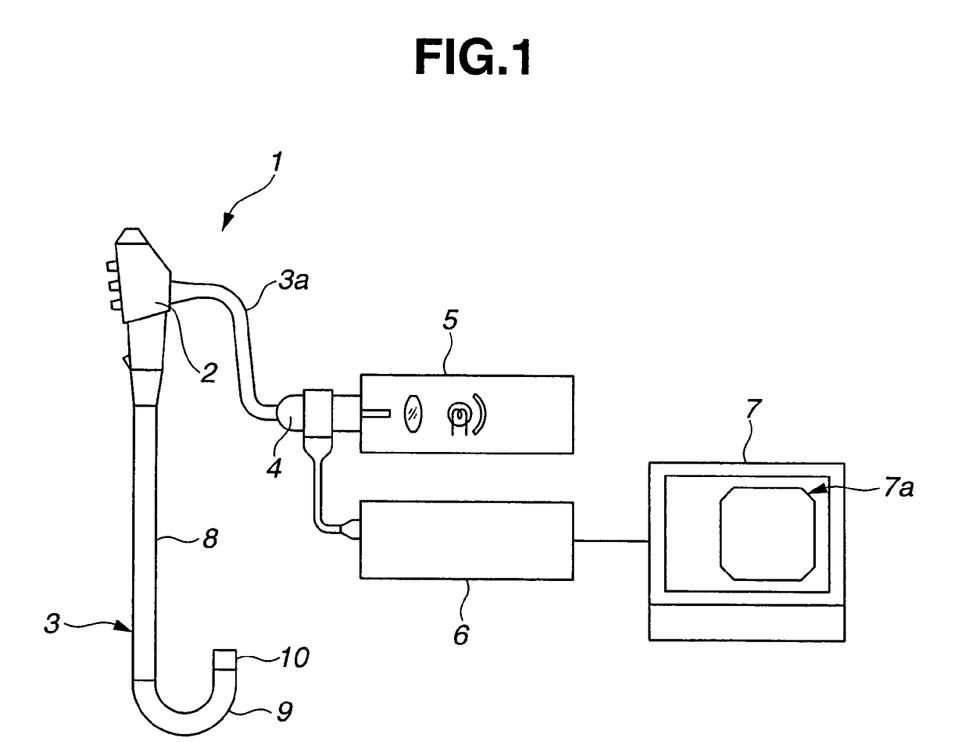
FIG. 1 is a whole configuration view of an endoscope apparatus.

As shown in FIG. 1, an endoscope apparatus according to the present embodiment includes an endoscope having a wide viewing angle (hereinafter simply referred to as "endoscope") 1, a light source device 5, a processor 6, and a monitor 7. An endoscope 1 includes an operation portion 2 for performing bending operation and control of various ducts, an insertion portion 3, of which proximal end side is connected to the operation portion 2, to be inserted into a body cavity, and a universal cord 3a including a connector portion 4 at a distal end thereof and extended from the operation portion 2. To the connector portion 4, the light source device 5 and the processor 6 are connected, and the monitor 7 is connected to the processor 6.

The insertion portion 3 of the endoscope 1 includes a flexible tube portion 8 having flexibility, a bending portion 9 provided at a distal end side of the flexible tube 8, and a distal end portion 10 provided at a distal end side of the bending portion 9. The distal end portion 10 includes a distal end surface formed in a shape of a cannonball, and an image-pickup unit 40 (See FIG. 3) built in inside thereof as an observation optical system.

Furthermore, the operation portion 2 includes an operation knob for bending the bending portion 9 by remote control, a push-button switch for performing various operations such as air/water supply, and the like.

The light source device 5 includes a light source for illumination and is connected with the operation portion 2, the insertion portion 3, and a light guide (not shown) provided inside the universal cord 3a via the connector portion 4. Furthermore, in the present embodiment, the light source device 5 contains an air/water supply source and a suction source to supply air and water to and perform suctioning through the ducts provided to the endoscope 1.

Figure 3:
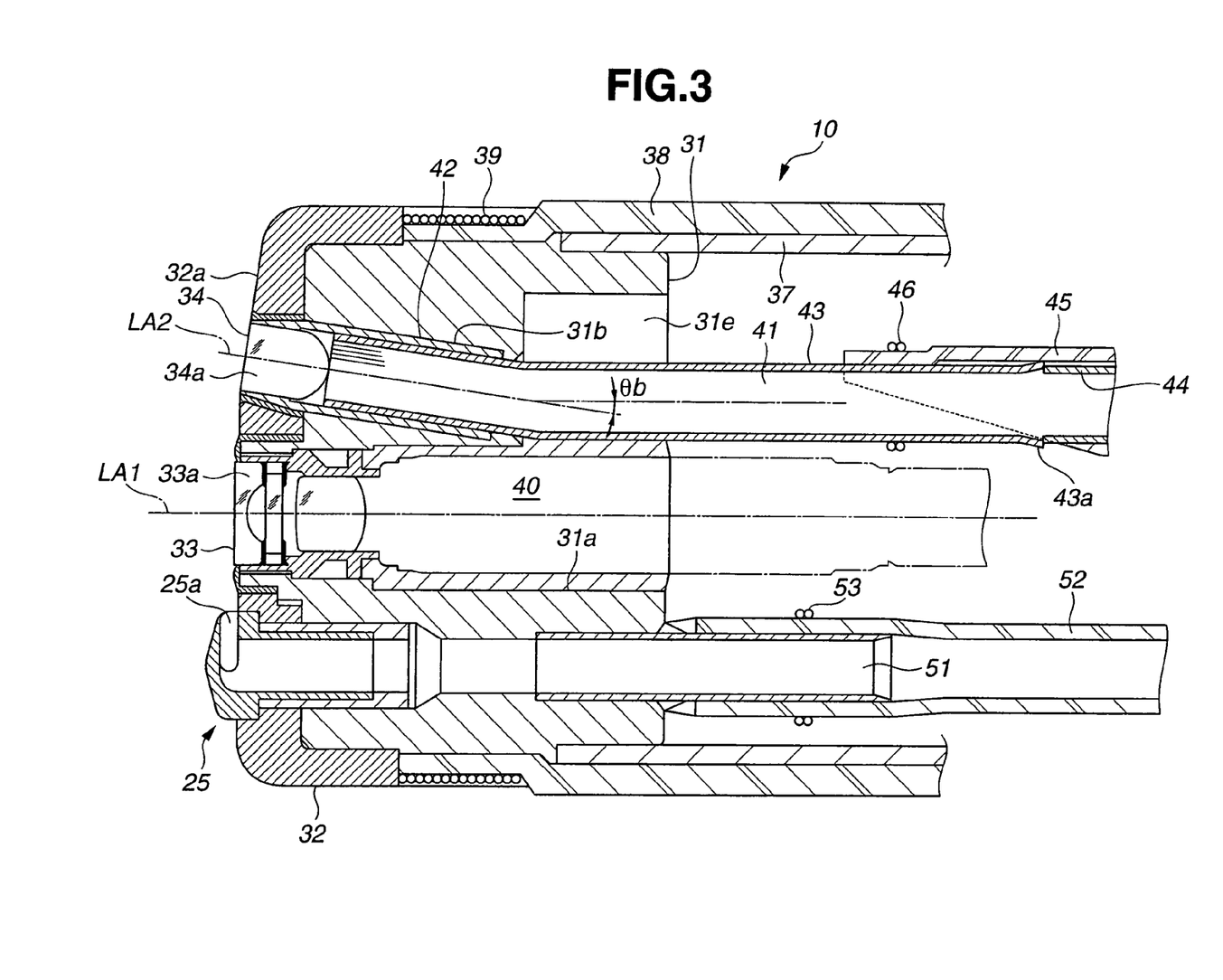
FIG. 3 is a cross-sectional view along III-III line of FIG. 2.
Figure 4:
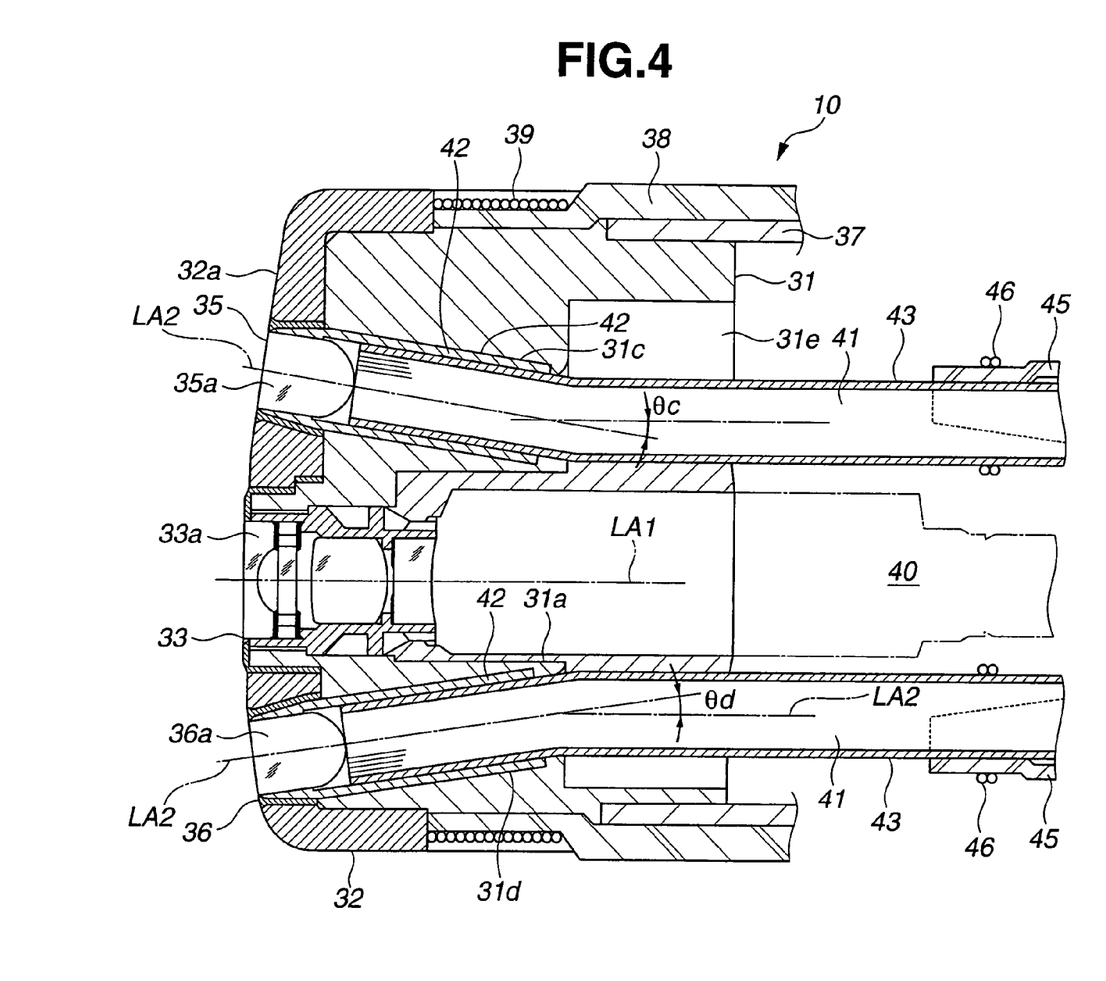
FIG. 4 is a cross-sectional view along IV-IV line of FIG. 2.

As shown in FIGS. 3 and 4, on a distal end side of the distal end portion 10 of the endoscope 1, a distal end rigid portion 31 is provided as the endoscope distal end portion. To a rear portion of the distal end rigid portion 31, a distal end portion of a bending distal end piece 37 is fixed, and the rear portion of the distal end rigid portion 31 and the bending distal end piece 37 are covered with an outer cover tube 38. In addition, the distal end of the outer cover tube 38 is fixed to the distal end rigid portion 31 by a thread winding 39.

Figure 2:
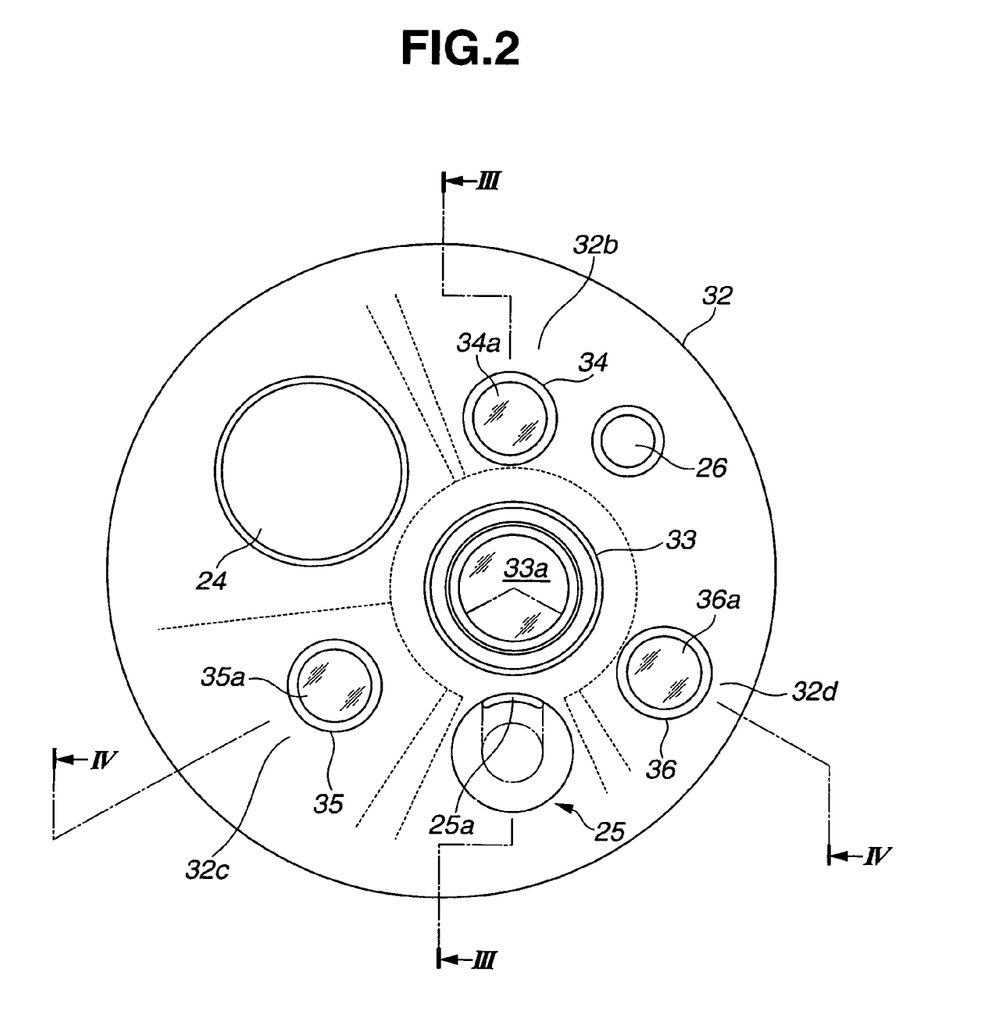
FIG. 2 is a front view of an endoscope distal end portion.

The distal end rigid portion 31 includes a distal end cap 32 attached and fixed to the distal end surface thereof. As shown in FIG. 2, the distal end cap 32 includes an observation window 33 open at a position slightly deviated to one side from the center of the distal end surface thereof. Around the observation window 33, a first to a third illumination windows 34 to 36 are open, respectively. Furthermore, a suction port 24 is open between the first illumination window 34 and the second illumination window 35. An air/water supply nozzle 25 is provided between the second illumination window 35 and the third illumination window 36. In addition, a forward water supply port 26 is provided between the first illumination window 34 and the third illumination window 36.

The observation window 33 has an objective lens 33a with wide viewing angle of approximately 140 to 210 degrees, and the illumination windows 34 to 36 have illumination lenses 34a to 36a, respectively. The air/water supply nozzle 25 cleanses stain of the objective lens 33a by supplying air and water from an opening portion 35a to the objective lens 33a. The forward water supply port 26 cleanses blood, mucus, and the like, at a diseased site in a body cavity by supplying water forward from the forward water supply port 26.

Figure 5:
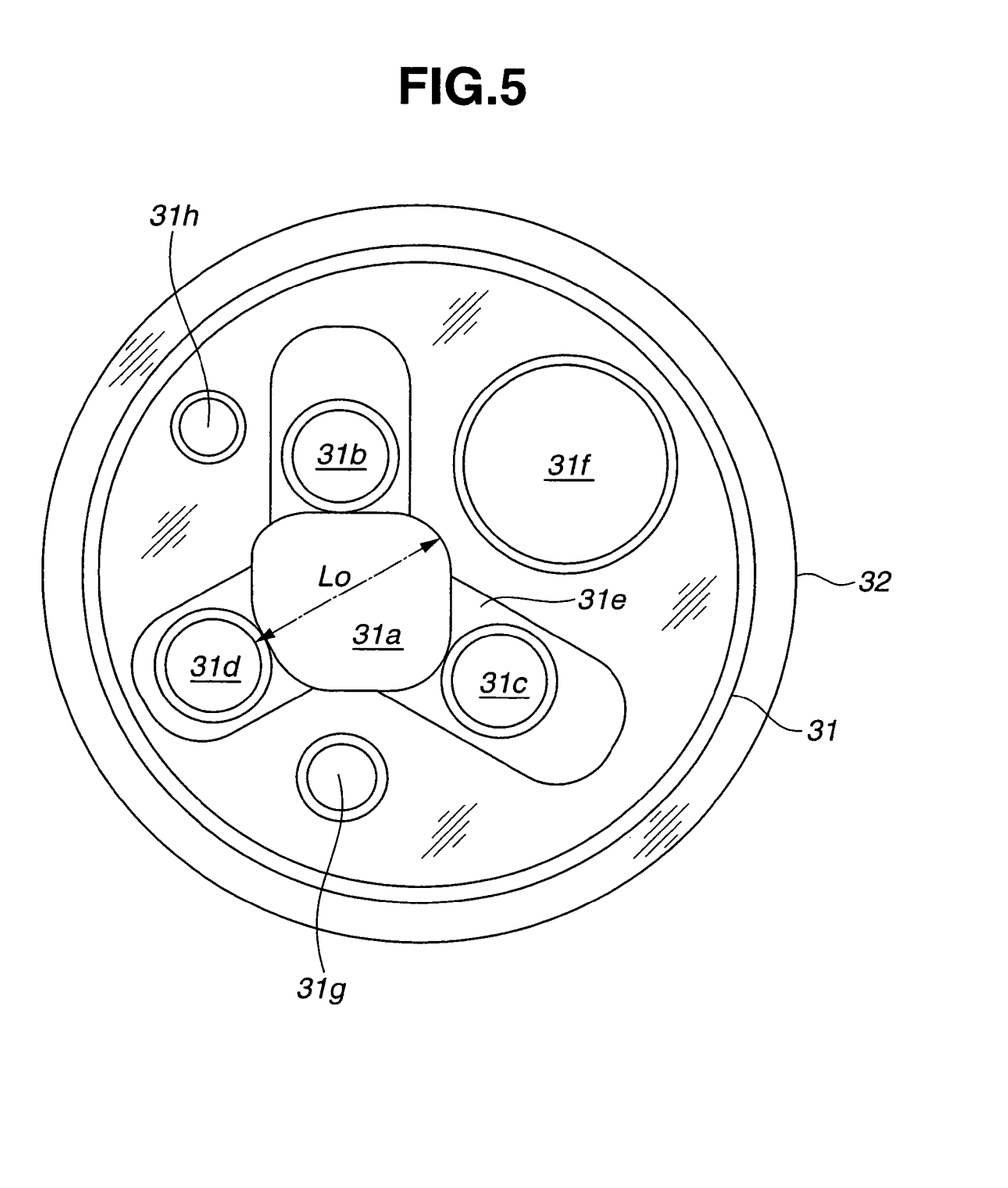
FIG. 5 is a rear view of a distal end rigid portion.
Figure 6:
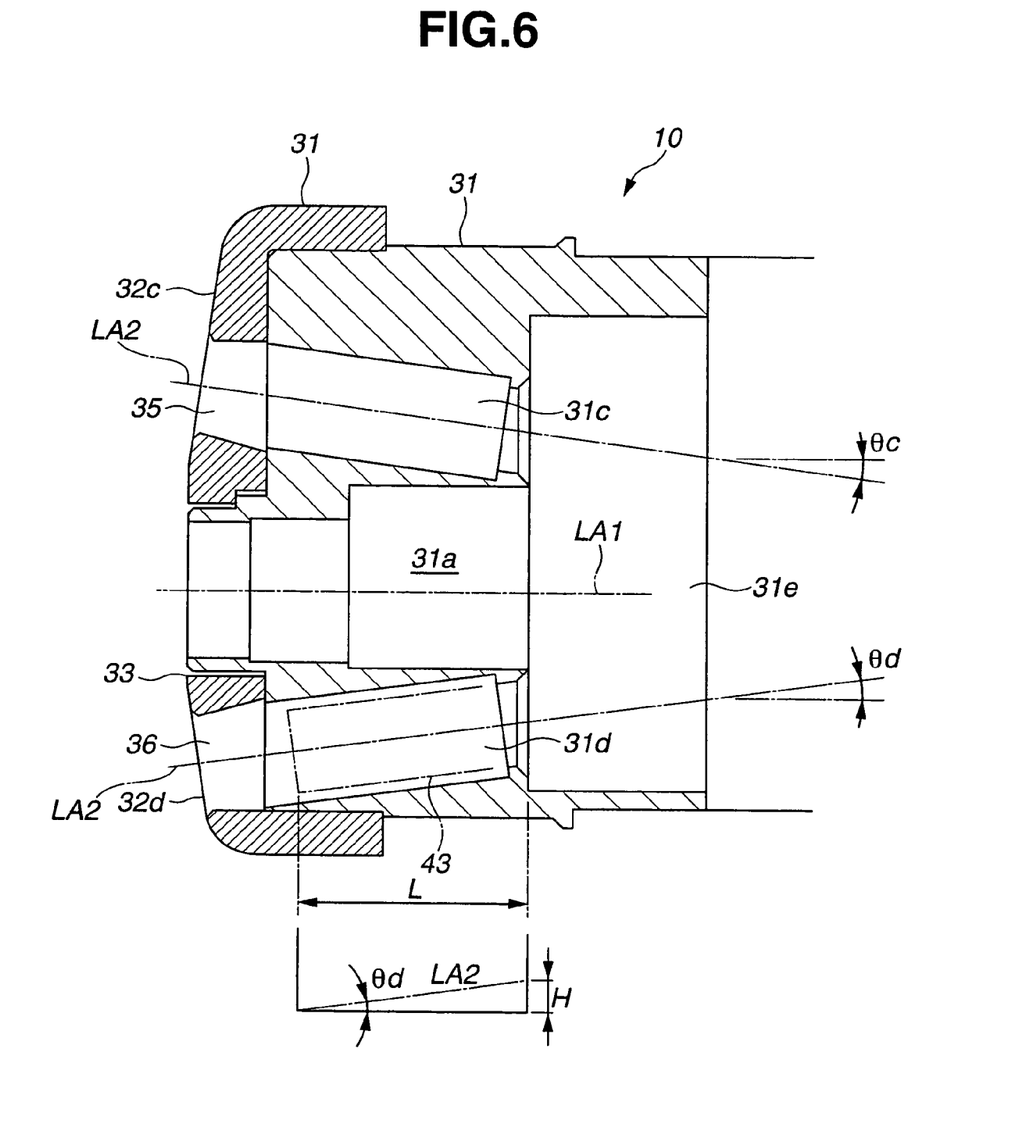
FIG. 6 is a cross-sectional view of the distal end rigid portion and a distal end cap of FIG. 4.

Furthermore, as shown in FIGS. 5 and 6, the distal end rigid portion 31 has an observation hole 31a formed so as to communicate with the observation window 33, and around the observation hole 31a, a first to a third illumination holes 31b to 31d are formed so as to communicate with the first to the third illumination windows 34 to 36, respectively. Furthermore, the distal end rigid portion 31 has a hole 31f for suction port communicating with the suction port 24, a hole 31g for air/water supply nozzle to which the air/water supply nozzle 25 is attached, and a hole 31h for forward water supply port to which the forward water supply port 26 is attached. Furthermore, on a back surface of the distal end rigid portion 31, a radial concave portion 31e is formed so as to be radiated from the observation hole 31a as a center and encircle the respective illumination holes 31b to 31d.

The observation hole 31a is formed such that a central axis LA1 thereof is along the insertion direction of the endoscope 1, and the hole 31f for the suction port, the hole 31g for the air/water supply nozzle, and the hole 31h for the forward water supply port are formed such that central axes of the respective holes are in parallel with the central axis LA1. On the other hand, the respective illumination holes 31b to 31d are arranged such that central axes LA2 of the respective holes incline outwardly by inclination angles of θb, to θd, respectively.

In addition, the image-pickup unit 40 is inserted into the observation hole 31a and fixed thereto by a fixing screw (not shown) screwed from a side surface of the distal end rigid portion 31. The image-pickup unit 40 has a distal end portion facing the observation window 33, and to the distal end portion, the objective lens 33a is fixed. In addition, the image-pickup unit 40 has an image-pickup element (not shown) such as CCD, CMOS, and the like, mounted at the rear of the objective lens 33a. Note that an endoscope image picked up by the image-pickup element provided to the image-pickup unit 40 is photoelectrically converted and transmitted to the processor 6 as an image signal. After a predetermined image processing is performed on the image signal in the processor 6, an observation image 7a is displayed on the monitor 7 (See FIG. 1).

The illumination holes 31b to 31d include a casing body 42 mounted respectively thereto, and the distal end cap 32 is fixed to the distal ends of the casing bodies with adhesive and the like. To the distal end portions of the respective casing bodies 42, the illumination lenses 34a to 36a are attached and fixed with adhesive and the like, respectively. Furthermore, in the respective casing bodies 42, the distal end surfaces of the light guide (LG) fiber bundles 41 come into contact with the rear portions of the illumination lenses 34a to 36a, respectively. Each of the LG fiber bundles 41 has a metal pipe 43 inserted through and held on the outer periphery of the distal end portion thereof and a flexible protective tube 44 externally fitted to the rear of the metal pipe.

The distal end of the metal pipe 43 containing the LG fiber bundle 41 is attached to the casing body 42 and fixed thereto by a fixing screw (not shown) screwed from the side surface of the distal end rigid portion 31. In addition, a rear end portion 43a of the metal pipe 43 is expanded in a trumpet-like shape, and with end surfaces of the rear end portion, the distal end of the protective tube 44 comes into contact. Therefore, the distal end of the protective tube 44 is locked by the rear end portion 43a of the metal pipe 43, which is expanded in a trumpet-like shape, thereby restricting the movement of the protective tube in the distal end direction.

Furthermore, a rear portion of the metal pipe 43 and the protective tube 44 are covered with an outer cover tube 45, and a distal end portion of the outer cover tube 45 is fixed to the metal pipe 43 by a thread winding 46. The distal end of the outer cover tube 45 is diagonally cut so as to facilitate the attachment to the metal pipe 43. Note that the respective LG fiber bundles 41 and the distal end portion of the respective metal pipes externally fitted to the LG fiber bundles 41 are bent respectively at angles of θb to θd degrees which are the same as the inclination angles of the respective casing bodies 42, and fixed to the respective casing bodies 42 while maintaining the inclination angles of θb to θd.

Illumination lights from the respective LG fiber bundles 41 are emitted forward at inclination angles of θb to θd with respect to the central axis LA1 of the image-pickup unit 40, respectively. Note that the inclination angles cover the viewing range of the image-pickup unit 40, and each of the inclination angles θb to θd is set according to the observation viewing angle of the image-pickup unit 40.

In addition, the surface of the distal end cap 32 on which the respective illumination windows 34 to 36 are open has tapered surfaces 32b to 32d approximately perpendicular to the respective central axes LA2. Furthermore, a coupling tube 51 is attached and fixed from backward to the hole 31g for the air/water supply nozzle of the distal end rigid portion 31, to which the proximal end side of the air/water supply nozzle 25 is attached, and to the coupling tube 51, a water supply tube 52 is connected. Moreover, a distal end portion of the water supply tube 52 is fixed to the coupling tube 51 by a thread winding 53.

Note that, though not shown, a suction channel serving also as a treatment instrument channel is connected to the hole 31f for the suction port provided to the distal end rigid portion 31. The suction channel is connected to the suction source provided to the light source device 5, via the insertion portion 3, the operation portion 2, the universal cord 3a, and the connector portion 4.

In addition, the LG fiber bundles 41 inserted in and held by the respective casing bodies 42 are tied in one LG fiber bundle in the middle of the insertion portion 3, and the tied LG fiber bundle is connected to the light source device 5 via from the operation portion 2 to the connector portion 4, to receive the illumination light from the light source for illumination built in the light source device 5 and transmit the received illumination light to the distal end side.

Next, description will be made on an operation of the endoscope 1 according to such a configuration. The illumination light emitted from the light source for illumination which is built in the light source device 5 is transmitted in the distal end direction of the endoscope by the single LG fiber bundle inserted in the universal cord 3a, the operation portion 2, and the insertion portion 3. The one LG fiber bundle is divided into three LG fiber bundles 41 in the middle of the insertion portion 3 of the endoscope, and a subject is illuminated with the light emitted forward of the endoscope 1 from each of the LG fiber bundles 41.

Then, the reflected light from the subject is received by the image-pickup element such as CCD, and CMOS provided to the image-pickup unit 40, and photoelectrically converted in the image-pickup element to be transmitted as an image signal to the processor 6. In the processor 6, a predetermined image processing is performed on the received image signal and an observation image 7a is displayed on the monitor 7.

Incidentally, in a case where there is a possibility that the LG fiber bundles 41 are damaged in the middle thereof, for example, in a case where the observation image 7a displayed on the monitor 7 becomes dark, or the observation image 7a is not displayed at all, light amount of the illumination light emitted from each of the LG fiber bundles 41, and the like, are inspected and presence or absence of the damage of the LG fiber bundles is checked. Then, when it is determined that the LG fiber bundles 41 are damaged, the LG fiber bundles are replaced.

In replacing the bundles, at first, the thread winding 39 which fixes the distal end of the outer cover tube 38 to the distal end rigid portion 31 provided to the endoscope distal end portion 10 is released, and the distal end of the outer cover tube 38 is pulled off backward to expose the inside of the endoscope distal end portion 10.

Next, the fixing screw (not shown) fixing the image-pickup unit 40 to the observation hole 31a of the distal end rigid portion 31 is removed from the side surface of the distal end rigid portion 31. After that, the image-pickup unit 40 is moved rearward (in the right direction in FIGS. 3 and 4) using a tool not shown and detached from the observation hole 31a and the radial concave portion 31e.

Then, by using a tool not shown, the LG fiber bundles 41 respectively inserted in the illumination holes 31b to 31d formed in the distal end rigid portion 31 via the casing bodies 42 and the metal pipes 43 attached to the outer periphery of the LG fiber bundles are moved one by one obliquely backward along the central axes LA2 of the respective illumination holes 31b to 31d to be pulled out.

At this time, the image-pickup unit 40 has been removed from the observation hole 31a and the radial concave portion 31e. Therefore, when the metal pipe 43 is moved obliquely backward, the metal pipe 43 can be smoothly withdrawn, because it is possible to secure the space after the removal of the image-pickup unit 40 as a space for withdrawal.

For example, in a case of withdrawing the LG fiber bundle 41 attached to the third illumination hole 31d and the metal pipe 43 attached around the bundle, as shown in FIG. 6, moving distance L required for the withdrawal of the bundle and the pipe in the direction along the central axis LA1 of the observation hole 31a is from the distal end of the metal pipe 43 to the radial concave portion 31e. In this case, moving distance H in the direction perpendicular to the central axis LA1 is expressed by the following formula, that is, $H = L \cdot \tan\theta d$.

Therefore, as shown in FIG. 5, distance Lo between the center of an inner periphery exposed on the bottom surface of the radial concave portion 31e of the third illumination hole 31d and the inner wall surface on an opposite angle of the observation hole 31a, which is distant from the illumination hole 31d, is secured to be longer than the moving distance H (H<Lo), so that it is possible to smoothly withdraw the LG fiber bundle 41 and the metal pipe 43 attached around the bundle from the third illumination hole 31d. Note that the same is true with the LG fiber bundles 41 attached to the other illumination holes 31b, 31c and the metal pipes 43 attached on the outer periphery of the bundles.

After the LG fiber bundles 41 and the metal pipes 43 attached on the outer periphery of the bundles are withdrawn from the respective illumination holes 31b to 31d, the LG fiber bundles are pulled out from the side of the connector portion 4 of the universal cord 3a of the endoscope 1.

Then, a new LG fiber bundle is sent from the connector portion 4 of the universal cord 3a of the endoscope 1 in the direction of the distal end portion 10, and the LG fiber bundle is divided into three at the distal end thereof and the respective divided LG fiber bundles 41 are attached to the casing bodies 42 attached to the illumination holes 31b to 31d, respectively. Note that the attachment procedure is performed in the order opposite to the above-described withdrawal procedure.

In this way, the present embodiment allows the LG fiber bundles 41 to be smoothly replaced, since, in replacing the LG fiber bundles, the image-pickup unit 40 is removed at first, then the space after the removal is utilized for a space for the withdrawal of the respective LG fiber bundles 41 and the metal pipes 43 attached on the outer periphery of the bundles.

Having described the preferred embodiments of the invention referring to the accompanying drawings, it should be understood that the present invention is not limited to those precise embodiments and various changes and modifications thereof could be made by one skilled in the art without departing from the spirit or scope of the invention as defined in the appended claims.

What is claimed is:

1. An endoscope comprising:
    an endoscope distal end portion for holding a light guide fiber bundle for guiding illumination light from a light source and an observation optical system for observing a subject illuminated with light emitted from the light guide fiber bundle, the endoscope distal end portion comprising:

a distal end rigid portion for holding the light guide fiber bundle and the observation optical system, the distal end rigid portion comprising:

an observation hole removably holding a distal end portion of the observation optical system, and an illumination hole arranged adjacent to the observation hole, and having a central axis inclining outwardly with respect to a central axis of the observation hole, the illumination hole linearly and removably holding a distal end portion of the light guide fiber bundle along the central axis inclining outwardly; and a concave portion formed on a back surface of the distal end rigid portion, the concave portion encircling the illumination hole with the observation hole as a center, wherein the central axis of the observation hole and the central axis of the illumination hole are arranged with respect to the concave portion such that the light guide fiber bundle is removed into a space in the concave portion along the central axis of the illumination hole, the space being occupied by the obervation optical system before the observation optical system is removed from the observation hole to the back surface side of the distal end rigid portion.

2. An endoscope according to claim 1, wherein the concave portion is secured to be larger than a moving extent of the light guide fiber bundle when inserting and withdrawing the distal end portion of the light guide fiber bundle.

3. An endoscope according to claim 2, the distal end portion of the light guide fiber bundle is formed to be bent in an inclined state.

4. An endoscope according to claim 1, the distal end portion of the light guide fiber bundle is formed to be bent in an inclined state.

* * * * *